United States Patent [19]

Dvorak et al.

[11] Patent Number: 5,781,891

[45] Date of Patent: Jul. 14, 1998

[54] MEDICAL TRANSCRIPTION SYSTEM WITH TEXT EXPANSION

[75] Inventors: Carl D. Dvorak; Anthony C. Brummel. both of Madison, Wis.

[73] Assignee: Epic Systems Corporation. Madison, Wis.

[21] Appl. No.: 593,223

[22] Filed: Jan. 29, 1996

[51] Int. Cl.$^6$ .................................................. G06F 17/28
[52] U.S. Cl. ............................................ 705/2; 707/534
[58] Field of Search ............................ 395/796, 753, 395/793; 705/2, 3, 1; 704/3; 707/531, 534

[56] References Cited

U.S. PATENT DOCUMENTS

| | | | |
|---|---|---|---|
| 4,396,992 | 8/1983 | Hayashi et al. | 395/796 |
| 4,650,349 | 3/1987 | Westreich | 395/796 |
| 4,969,097 | 11/1990 | Levin | 395/796 |
| 5,623,406 | 4/1997 | Ichbiah | 395/753 |

OTHER PUBLICATIONS

Microsoft Word for Windows, User's Reference, Microsoft Corporation, 1988-99, pp. 141 and 142.

*Primary Examiner*—Donald E. McElheny, Jr.
*Attorney, Agent, or Firm*—Quarles & Brady

[57] ABSTRACT

A simplified method of storing and invoking standard phrases during text entry to an electronic computer allows a phrase to be recalled by typing an abbreviated phrase name preceded by a predetermined character string selected from characters of a standard typewriter keyboard, eliminating the interruption typing often incident to finding special function keys. The character string is selected to be unambiguously distinguishable from standard entered text.

9 Claims, 3 Drawing Sheets

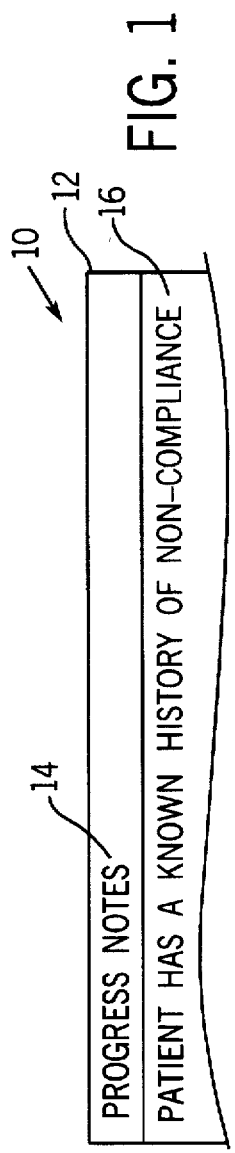
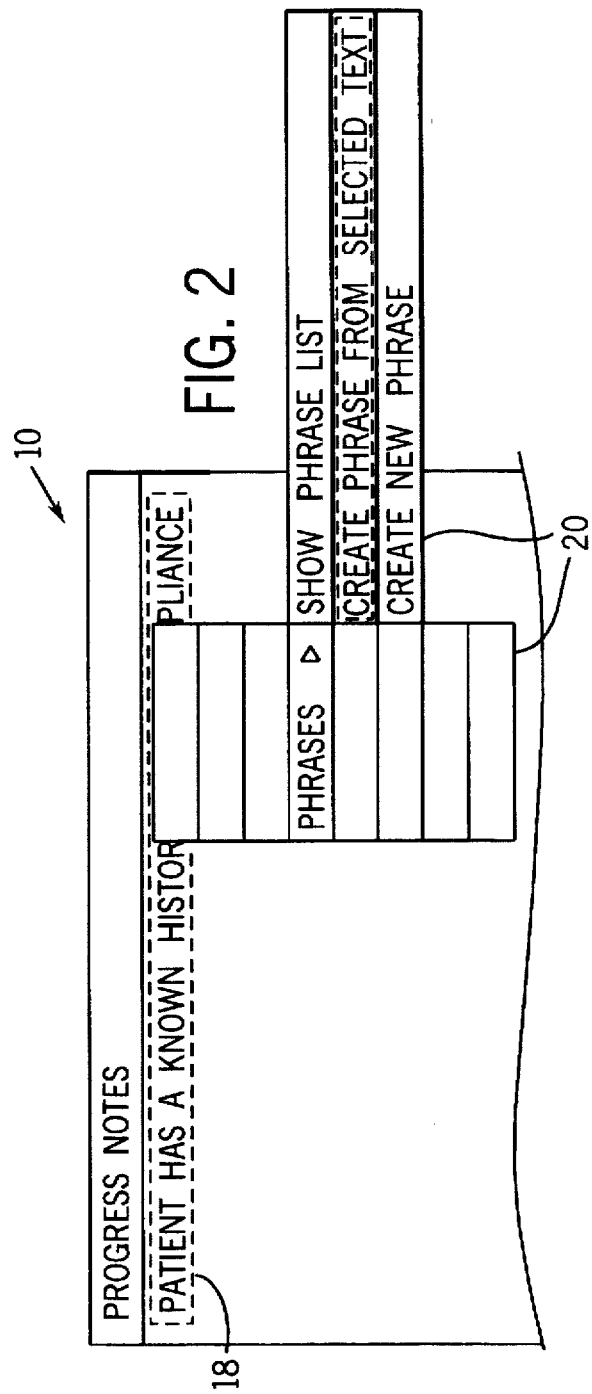

FIG. 3
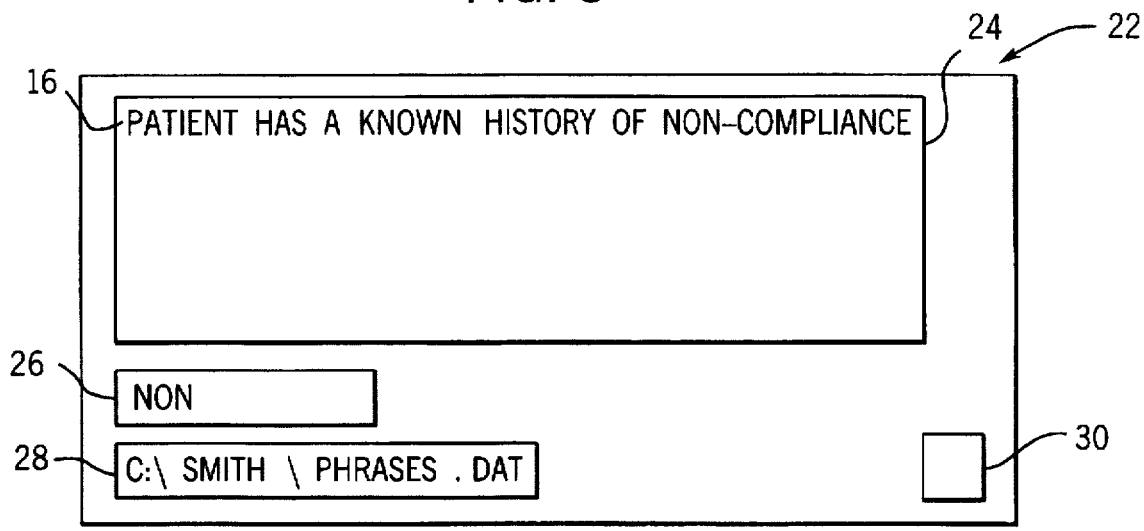
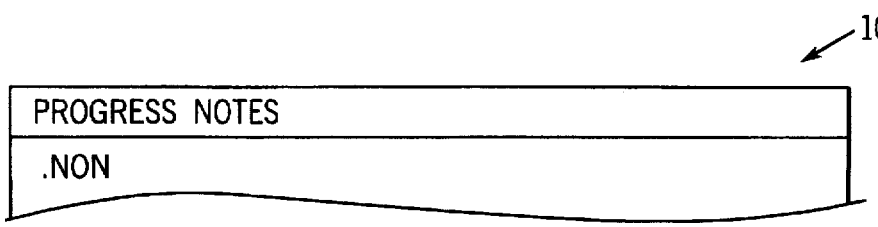
FIG. 4
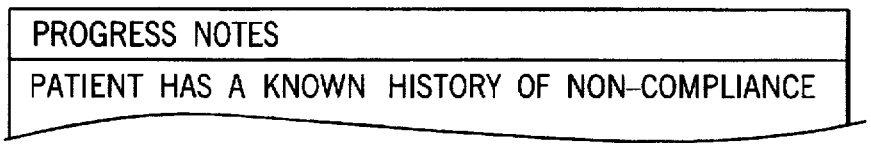
FIG. 5

5,781,891

MEDICAL TRANSCRIPTION SYSTEM WITH TEXT EXPANSION

FIELD OF THE INVENTION

The present invention relates generally to computer programs for text entry and in particular to a program allowing faster entry of standard textual information.

BACKGROUND OF THE INVENTION

Physicians, in maintaining patient records, ordinarily prepare summaries of patient visits or treatments. Although these summaries may be dictated by the physician for later transcription, often the physician types these summaries directly into a computer system, in order to avoid transcription errors, delay, and the additional cost of transcription services. In these circumstances, it is desirable to simplify the process of typing the summaries as much as possible.

In a particular practice area, there will be common phrases used in identical form in many different summaries. Ideally these phrases could be entered without typing the entire phrase. For this purpose, some word processors allow the user to develop glossaries of commonly used phrases. Each phrase may be associated with a shorter phrase name which may be an abbreviation or even a short word that provides a mnemonic for the phrase. The typist enters the shorter phrase name and then by pressing a special command key, causes the phrase name to be replaced by the longer phrase.

For the inexperienced typist, the requirement that a special function key be pressed is cumbersome and by interrupting the normal stream of typing may eliminate some of the speed advantages of the glossary system. Nevertheless, without a special function key, the word processor may interpret normal text as a phrase name and cause unintended and unexpected errors in the transcription.

SUMMARY OF THE INVENTION

The present invention provides a system for text entry that identifies phrase names, (representing longer phrases to be substituted into the text) by means of short character strings selected from the keys found on a standard typewriter. By eliminating the need for the typist to use non-standard function keys or an extra-keyboard device such as a mouse, the flow of typing is not interrupted. The character strings used to delimit the phrase name are selected so that they do not occur in ordinary written text and thus so that there is no danger of unintended text substitution.

Specifically, the present invention provides a computer program for transcription on an electronic computer communicating with a computer memory and an alphanumeric keyboard and a computer display. The program instructs the computer to receive a transcription including a series of characters from the keyboard. As the characters are entered, they are monitored for a predetermined string of characters. When this predetermined string is detected, a subset of that string is matched to one of a library of phrase names stored in memory and associated on a one-to-one basis with a longer phrase also stored in memory. As the transcription is stored in computer memory predetermined string of characters is replaced with the phrase.

Thus it is one object of invention to allow the rapid entry of a phrase name during typing without requiring the use of special keys whose position may be unfamiliar to typists trained with the standard QWERTY keyboard.

The predetermined string of alphanumeric characters may be a period followed by any non space character.

Thus, it is another object of the invention to select as a phrase name identifier, a string of standard keyboard characters that will not occur during normal text entry. In normal text entry, a period is correctly only followed by a word terminating character (a space, punctuation, or "enter" command) and thus the combination of a period and non space character robustly identifies the beginning of a phrase name.

The computer program may monitor the transcription for a first and second predetermined string of delimiting characters. After both delimiting strings have been detected, a subset of the strings and the intervening characters is matched to a phrase name stored in memory, the phrase name being linked to longer phrase. The first delimiting string and intervening characters are replaced in memory by the phrase. The last character of the second delimiting string is preserved in memory.

Thus, it is another object of the invention to provide maximum flexibility in choosing phrase names as mnemonics of longer phrases. The use of two delimiting strings selected from standard typewriter characters identifies a phrase name of arbitrary length from normal text-even if it is an ordinary word.

The second delimiting string may be a word terminating character such as a space character, and enter character or a punctuation character.

Thus it is yet another object of the invention to eliminate the need for the user to consciously identify the end, of the phrase name or take any further action after the beginning of the phrase name is indicated by the first delimiter. The user will naturally provide the word terminating character after entry of the phrase name. The risk that common word terminating characters will be misinterpreted is eliminated by the requirement that the second delimiter only be detected after the first delimiter is received.

The foregoing and other objects and advantages of the invention will appear from the following description. In this description, reference is made to the accompanying drawings which form a part hereof and in which there is shown by way of illustration the preferred embodiment of the invention. Such embodiment does not necessarily represent the full scope of the invention, however, and reference must be made therefore to the claims for interpreting the scope of the invention.

BRIEF DESCRIPTION OF THE DRAWINGS

FIG. 1 is an example computer display generated by the program of the present invention as text is entered into a computer executing the program;

FIG. 2 is a display similar to FIG. 1 after entered text has been selected and the user has instructed the program to create a phrase from the selected text;

FIG. 3 is a different display generated by the program of the present invention during entry by the user of a phrase name and a phrase library name;

FIG. 4 is a display similar to that of FIG. 1 showing entry of a phrase name by a user after a first delimiting characters string but before a second delimiting character string;

FIG. 5 is a display similar to that of FIG. 4 showing the replacement of the phrase name by the phrase after the second delimiting character string has been entered.

DETAILED DESCRIPTION OF THE PREFERRED EMBODIMENT

Figure 6:
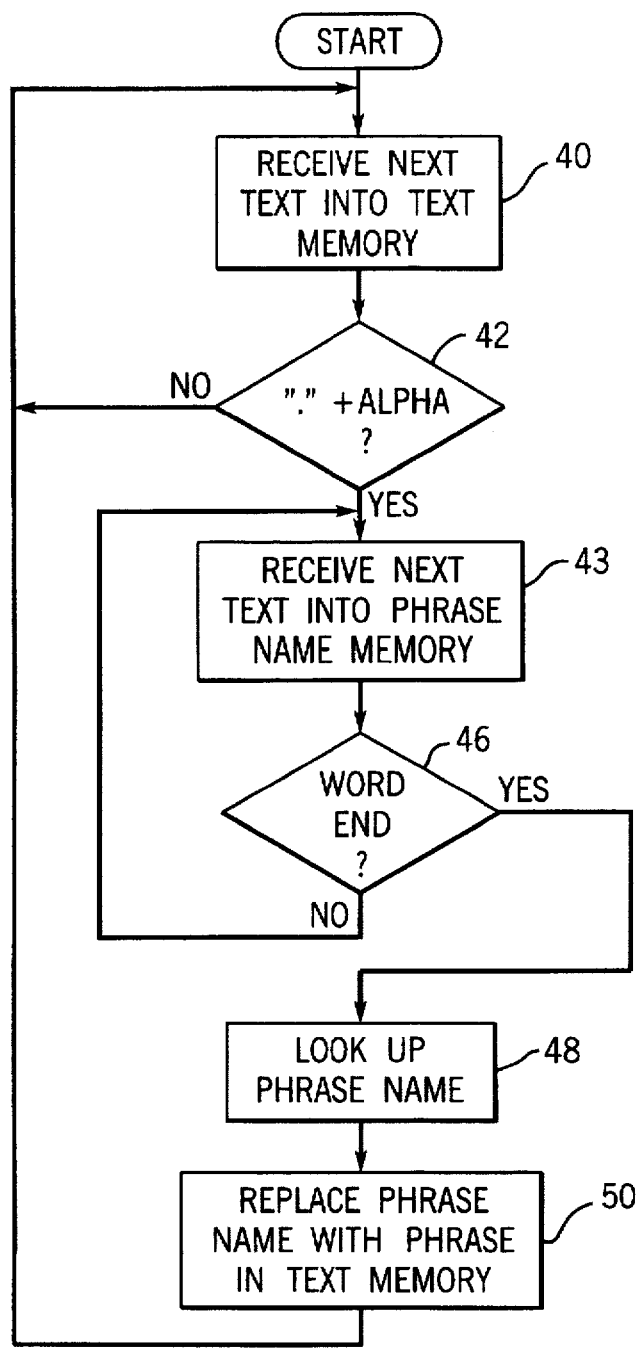
FIG. 6 is a flow chart depicting the operation of the program of the present invention during the text entry of FIGS. 4 and 5.

The program of the present invention provides a set of instructions that may be executed on a conventional electronic computer, for example, an IBM-compatible desktop computer well known in the art. Such a computer system includes an electronic microprocessor electrically connected with computer memory, typically a combination of solid state memory devices and one or more magnetic disk storage units. The microprocessor may provide output data to a printer or computer display, the latter displaying text or graphics according to instructions from the microprocessor as it executed a program. The microprocessor may also receive input data from a keyboard and a cursor control device such as a mouse or track ball. The keyboard may include character keys, allowing input of alphanumeric characters and various punctuation marks and symbols, and function keys not assigned to a character but providing commands to the computer. Henceforth the term character will refer to printing characters found on a standard typewriter keyboard. Such computers are now well known in the art.

The computer may include a standard text editor program allowing entry of text data into the computer memory and the display of the same on the display. The editor also provides the ability to edit the data, that is replace data with other data based on user commands. The present invention contemplates use with a text editor allowing use of the cursor control for controlling the position of a cursor on the display with respect to displayed text and thereby controlling the insertion point of text within a memory. The cursor control device may be further used to select text stored in memory by moving the cursor across the particular text with a function key, typically on the cursor control device, depressed. The program of the present invention supplements such a standard text editor. The operation of such text editors is well known in the art.

Referring now to FIG. 1, a sample screen display 10 generated by such a text editor provides a text frame 12 in which text is displayed upon entry into the computer. The frame may include a title block 14, in this case titling the frame as "Progress Notes. The frame 12 and title block 14 create a working space simulating a blank sheet of paper onto which notes may be recorded.

Text 16 may be entered into the frame 12 via the keyboard of the computer. In this case, the phrase "Patient has a known history of noncompliance" has been entered. As will be understood to those of ordinary skill in the art, the displayed text is also stored in computer memory.

Referring to FIG. 2, the text 16 may be placed into a phrase library for future use by selecting it, as indicated by a highlighting 18 depicted as a dotted line. The selection process, which normally identifies the text by a field reversal in which the text background become dark and the text characters become light, in contrast to their normal depiction, identifies a starting and ending location of the text as stored in computer memory. Such identification may be done by pointers, separate values stored in memory that describe starting and ending memory locations of the stored text corresponding to that highlighted on the display. In the preferred embodiment, the selection is accomplished by sweeping the cursor across the image of the desired text on the display, while a function key is depressed, a technique known in the art.

The selected text is placed in a library of phrases by a command from the user entered via the keyboard, or as depicted, by maneuvering the cursor over a set of menus 20 and pressing a function key when the cursor is positioned over the desired command listed on the menu. In this case the command is: "Create Phrase from Selected Text".

Referring to FIG. 3, upon entry of the command, a new screen display 22 is generated, this display 22 including: a text field 24 displaying the selected text 16 that will be converted into a reusable phrase, a phrase name entry field 26 for entry of a phrase name to be associated with the phrase, and a phrase library name entry field 28 where the user may specify one of several libraries into which the phrase and phrase name will be placed.

At this display 22, the user enters a phrase name into the phrase name field 26 by placing the cursor at that field 26 and typing the name on the key board. The phrase name may be an arbitrary string of alphabetic characters up to 255 characters in length. The phrase name may be an English word but may not have as its first character a number, for reasons that will be explained. Thus the user may select a name that may be easily remembered and associated with the phrase that it will invoke.

In this example, the phrase name "non" has been selected to stand for the phrase: "Patient has a known history of noncompliance".

At this display 22 the user may also select a library name from one or more available library names by placing the cursor at that field 28 and selecting one of the libary names displayed. A default library name is provided so the user need not enter a select a library name if a standard default library is acceptable.

In this example, the library name is: "C:\SMITH\PHRASES.DOC. " and is in the form of a standard DOS file name. As such the library name identifies a data file stored in computer memory (disk memory). In this example, the library is stored on a physical drive "C" under the directory name "Smith" in the library name of "Phrases". As such the library is non-volatile and will be preserved even if computer power is shut off.

The text 16 and the phrase name may at this time be edited by the user according to standard editing conventions, e.g., by moving the cursor to the appropriate position and deleting or inserting text. If the data in fields 24, 26, and 28 are correct as entered, an acceptance command is given, in this case by positioning the cursor over a virtual button 30 and pressing a command key.

Upon acceptance, the phrase name and phrase are stored in the portion of computer memory reserved for the library in a form so that each phrase name may be uniquely identified to a particular phrase. The phrase names may be alphabetized or indexed for rapid searching according to methods known in the art.

The user may repeat the process described with respect to FIGS. 1-3 to generate a multi-entry library in computer memory.

Referring now to FIG. 4, the screen display of FIG. 1 is shown again at the beginning of a subsequent text entry session. During this text entry session, the user may recall any phrase previously entered into a library by typing the phrase name as delimited by phrase name delimiters constructed of short strings of standard typewriter characters. Thus the phrases may be recalled without the need to remove ones fingers from the limited set of standard typewriter keys which are better known to casual typists.

Specifically the user may recall text 16 of "Patient has a known history of noncompliance" by typing a period followed by the phrase name "non" followed by any character that indicates the end of a word, such as a space, an enter key (the latter being the pressing of an enter key found on many computer keyboards and serving essentially the same function as a carriage return), or any punctuation mark, such as a hyphen, a comma, a colon, a semicolon, or another period. In this case the first phrase name delimiter is a period followed by any alphabetic character, and the second delimiter is the word terminating character. In both cases all of the characters that need to be typed by the user are standard alphabetic and punctuation-type characters common to all QWERTY keyboards and do not require access to nonstandard function "control" or "alt" keys found on many computer keyboards and not used for normal typing.

The delimiters serve to indicate to the computer program that the text between the delimiters is to be treated specially as a phrase name and not simply entered into computer memory with the other text. The period of the first delimiter must be followed by an alphabetic character to eliminate confusion between the delimiter and decimal fractions such as 0.25 which could occur in standard text.

Upon receipt of a word end character as shown in FIG. 5, the phrase associated with the phrase name replaces both the phrase and the leading period in computer memory and on the computer display. Thus, the characters used to delimit the phrase name from standard text are initially displayed, to eliminate ambiguity to the user, but ultimately replaced without a trace. The only exception to this replacement is the second delimiter and specifically the word termination character. This character is preserved in keeping with the intent that the second delimiter be automatic to the user as simply a natural entry after the phrase name. Thus, this entry after the phrase name, for example a space or punctuation, should be preserved.

Referring now to FIG. 6, the operation of the present invention in expanding a phrase name into a phrase occurs as part of a continuing review of text received from the keyboard. Referring to process block 40, at a first step in this process, new text typed by the user is received into text memory and displayed on the display. At decision block 42, the new text is reviewed to detect a text string corresponding to the first delimiter. In this case, the text string detected is a period followed by any alphabetic character. If there is no period followed by an alphabetic character, such as would indicate a phrase name, the program loops back to process block 40 to receive more text. In a typical text entry session with no phrase names used, the loop around process blocks 40 and decision block 42 continues until all the text has been entered. It will be understood that process block 40 includes additional tests for function keys and the like necessary to control the general editing process.

If at decision block 42, a period followed by an alphabetic character is detected, as indicated by process block 43, the period and alphabetic character are stored into a phrase memory, being a particular portion of the computer memory. Additional text entered after detection of the period and the alphabetic character continues to be placed into the phrase name memory per process block 43 until a second delimiter, a word terminating character, is detected at decision block 46. It will be understood by those of ordinary skill in the art that separate phrase memory distinct from the text memory is not required, but that the phrase name memory may in fact consist of pointers designating portions of the text memory. The use of this second delimiter allows the phrase name to be an arbitrary length and allows different phrase names that are subsets of each other, for example, "non" or "none." The ability of the second delimiter to be a common word terminating character relies of the fact that the second delimiter is not looked for until after the first delimiter has been detected.

When the second delimiter is detected at decision block 46, the program proceeds to process block 48 and the previously stored phrase names in the currently named library are searched to find a match between the character string stored in the phrase name memory between the period and the word terminating character and a phrase name in the library. If no corresponding phrase name is detected, an error message is provided to the user and no change is made in the text stored in text memory.

At process block 50, if the phrase name is located in the current library, the characters stored in the phrase name memory, including the initial delimiter of a period but excluding the final delimiter of a word terminating character, are located in the text memory, removed and replaced by the phrase associated with the matched phrase name.

In this way, entry of the phrase is a completely intuitive operation to a standard keyboard user who simply types a period and the abbreviated phrase name and can expect the phrase to be inserted seemingly into the advancing text.

The ease of generating a standard phrase to be stored in the phrase table and in invoking this phrase during normal typing significantly improves the efficiently of most unskilled typists who may be uncertain as to the location of special function keys, but who generally know the location of the alphabetic keys and associated punctuation marks. The use of normal typewriter characters as delimiters for phrase names is made possible by the recognition that simple combinations of characters are unlikely to occur in regular text entry.

The above description has been that of a preferred embodiment of the invention. It will occur to those that practice the art that many modifications may be made without departing from the spirit and scope of the invention. In order to appraise the public of the various embodiments that may fall within the scope of the invention, the following claims are made.

I claim:

1. A computer program for transcription on an electronic computer communicating with computer memory and a keyboard and a computer display, the program instructing the computer to:

(1) receive a transcription including a series of characters from the keyboard;

(2) monitor the series of characters for a predetermined non-space character prefix;

(3) when the predetermined non-space character prefix is detected, match at least a subset of a string of subsequent characters to one of a library of phrase names stored in memory, each phrase name linked to a longer phrase also stored in memory; and (4) store in computer memory the transcription of a series of characters replacing the predetermined string of characters with the phrase.

2. The computer program of claim 1 wherein the characters are those found on a standard typewriter.

3. The program of claim 1 wherein the predetermined string of characters is a period followed by any non-space character.

4. The program of claim 1 wherein there are multiple libraries of phrase names and phrases stored in memory each associated with a library name and wherein the program additionally instructs the computer to receive from the user a name of a library stored in memory; and wherein in operation (3) the computer uses the library named by the user.

5. The program of claim 1 wherein the characters of the transcription are displayed on the computer display as they are received and wherein the program also instructs the computer at operation (4) to replace the predetermined string of characters displayed on the display with the phrase.

6. A computer program for transcription on an electronic computer communicating with computer memory and a keyboard and a computer display, the program instructing the computer to:

(1) receive a transcription including a series of characters from the keyboard;

(2) monitor the series of characters for a at least one predetermined non-space delimiting character;

(3) upon detection of the predetermined non-space delimiting character, monitor the series of characters for at least one second predetermined delimiting character;

(4) when the second predetermined delimiting character is detected, match intervening characters to a phrase name in a library of phrase names stored in memory, each phrase name linked to a longer phrase of characters also stored in memory; and (5) store in computer memory the transcription replacing the first predetermined delimiting string of characters and the intervening characters with the longer phrase.

7. The computer program of claim 6 wherein the second predetermined delimiting character is a word terminating character and wherein at operation (5) the word terminating character is not replaced.

8. The program of claim 7 wherein the second predetermined delimiting character is a single character selected from the group consisting of: a space character, an enter character or a punctuation character.

9. The program of claim 6 wherein the first predetermined delimiting non-space character is a period followed by any non-space character.

* * * * *